United States Patent
Jin et al.

(10) Patent No.: US 7,759,101 B2
(45) Date of Patent: Jul. 20, 2010

(54) GINSENOSIDE GLYCOSIDASES HYDROLYZING GINSENOSIDE SUGAR MOIETIES AND USES THEREOF

(75) Inventors: Fengxie Jin, Qinggong-yuan No. 1, Ganjingzi-Qu, Dalian, Liaoning Province 116034 (CN); Hongshan Yu, Liaoning Province (CN)

(73) Assignee: Fengxie Jin, Liaoning Province (CN)

( * ) Notice: Subject to any disclaimer, the term of this patent is extended or adjusted under 35 U.S.C. 154(b) by 781 days.

(21) Appl. No.: 10/250,354

(22) PCT Filed: Dec. 29, 2000

(86) PCT No.: PCT/CN00/00744

§ 371 (c)(1),
(2), (4) Date: Jun. 30, 2003

(87) PCT Pub. No.: WO02/053722

PCT Pub. Date: Jul. 11, 2002

(65) Prior Publication Data

US 2004/0028671 A1   Feb. 12, 2004

(51) Int. Cl.
*C12N 9/52* (2006.01)

(52) U.S. Cl. .................. 435/200; 435/183; 435/195; 435/52; 435/72; 435/78

(58) Field of Classification Search ............... 435/207, 435/200, 183, 195, 52, 72, 78
See application file for complete search history.

(56) References Cited

FOREIGN PATENT DOCUMENTS

| | | | |
|---|---|---|---|
| CN | 1144847 A | | 3/1997 |
| CN | 1229086 A | | 9/1999 |
| GB | 2 179 042 A | | 2/1987 |
| RU | 2046140 C1 | | 10/1995 |

*Primary Examiner*—Irene Marx
*Assistant Examiner*—Susan Hanley
(74) *Attorney, Agent, or Firm*—Occhiuti Rohlicek & Tsao LLP

(57) ABSTRACT

The invention relates to ginsenoside glycosidases which hydrolyzes ginsenosides having higher contents in ginsengs so as to prepare rare ginsenosides with high physiologeical activity. Said ginsenoside glycosidases are derived from microorganism cultures, ginseng plants, almonds, wheat brans, malts and animal livers etc., and are categorized to four types depending on their capability of hydrolyzing the sugar moieties of ginsenosides, namely, ginsenoside glycosidase I, ginsenoside glycosidase II, ginsenoside glycosidase III and ginsenoside-α-rhamnosidase. The invention also relates to the uses of the ginsenoside glycosidases in preparing rare ginsenosides.

16 Claims, 4 Drawing Sheets

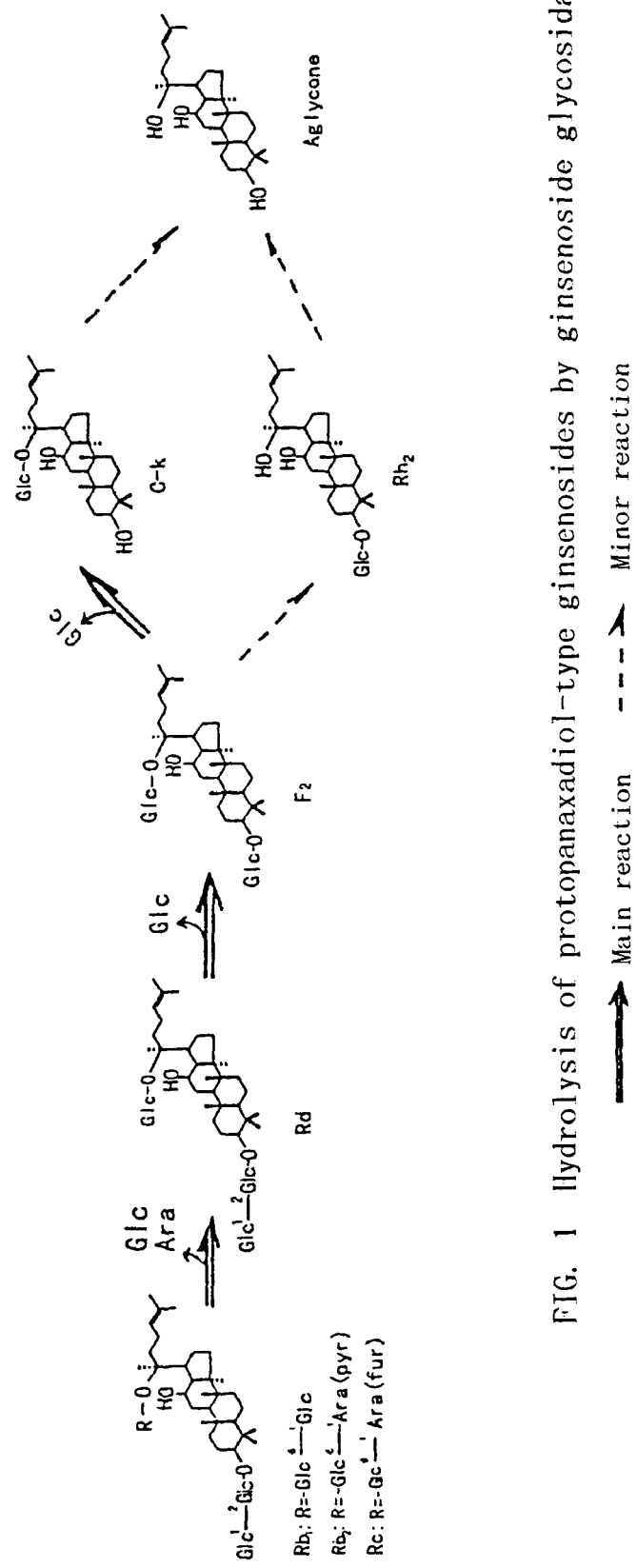
FIG. 1 Hydrolysis of protopanaxadiol-type ginsenosides by ginsenoside glycosidase I

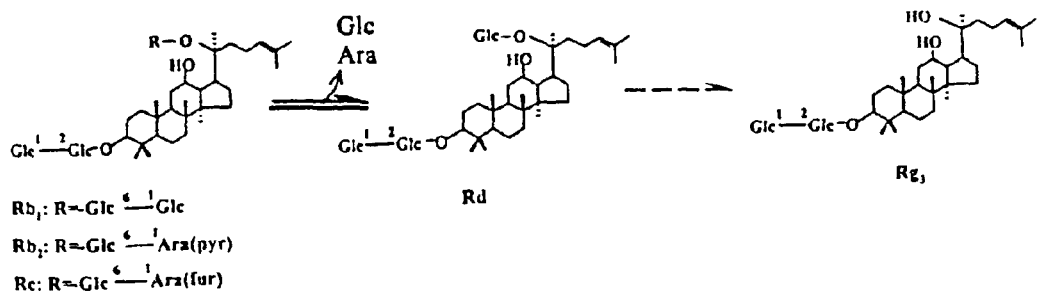
FIG. 2  Hydrolysis of protopanaxadiol-type ginsenosides by ginsenoside glycosidase II
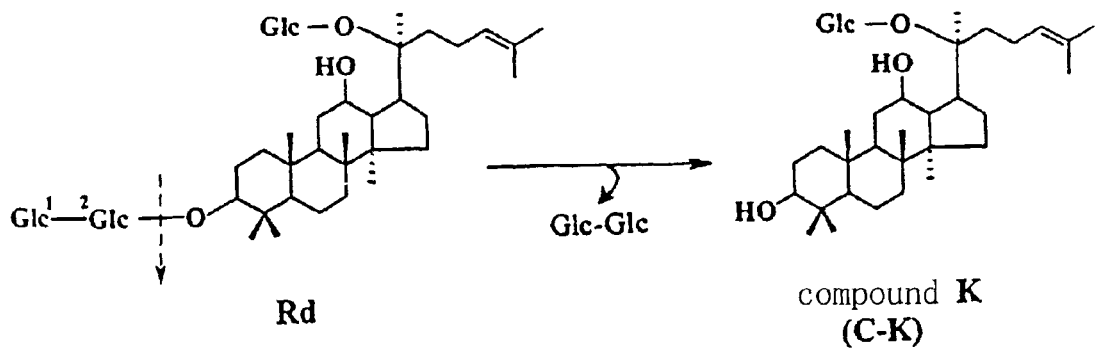
FIG. 3  Hydrolysis of protopanaxadiol-type ginsenosides by ginsenoside glycosidase III

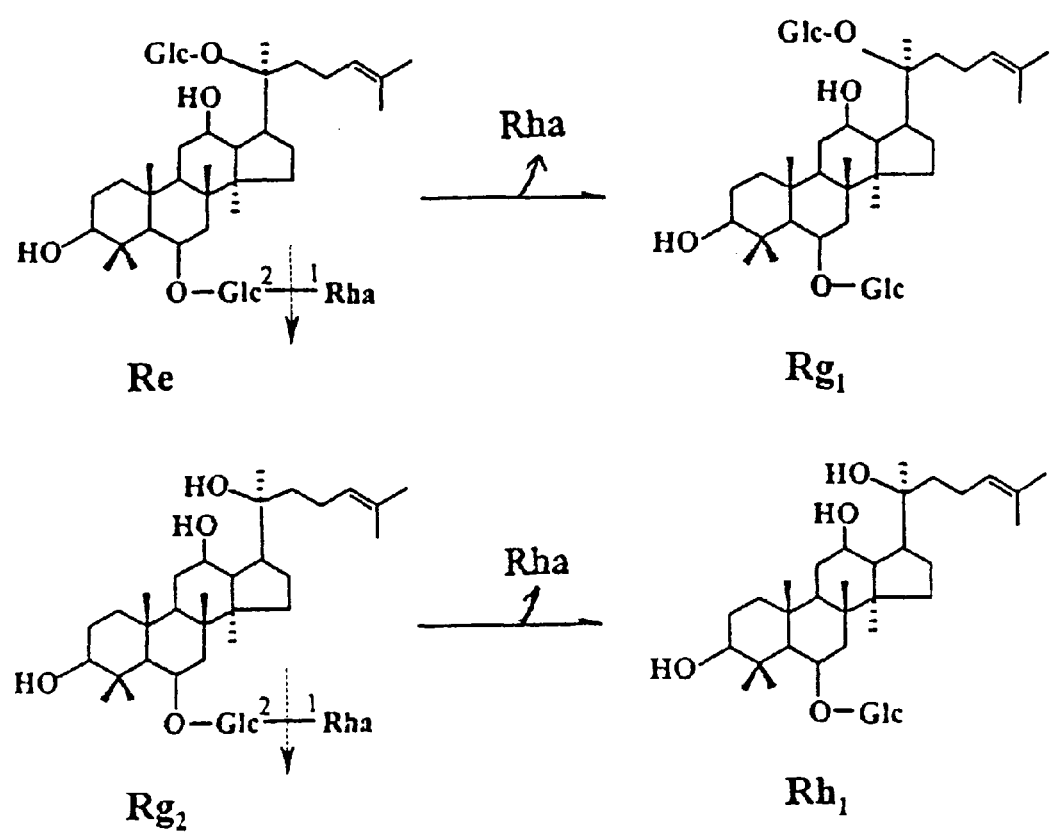
FIG. 4 Mechanism for hydrolysis by ginsenoside-α-rhamnosidase

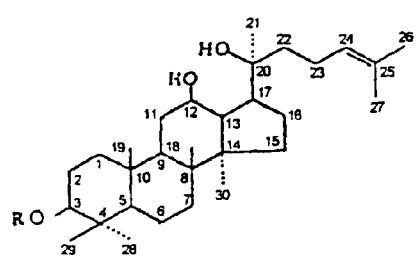
20(S)
Rg₃: R, β-Glc-(1→2)-β-Glc
Rh₂: R, β-Glc
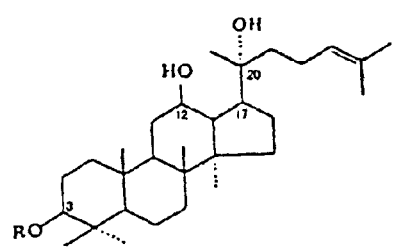
20(R)
Rg₃: R, β-Glc-(1→2)-β-Glc
Rh₂: R, β-Glc
20(S)
Rg₂: R, α-Rha-(1→2)-β-Glc
Rh₁: R, β-Glc
20(R)
Rg₂: R, α-Rha-(1→2)-β-Glc
Rh₁: R, β-Glc
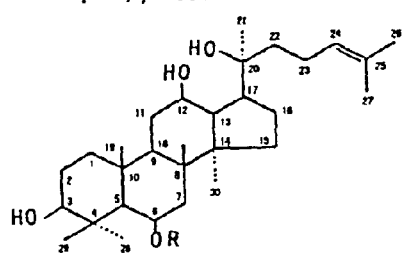
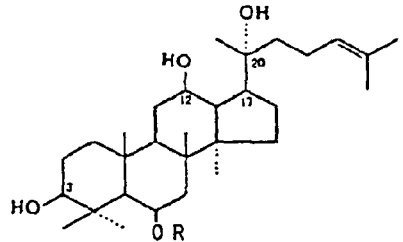
FIG. 5  Structures of 20(S)- and 20(R)-ginsenoside

GINSENOSIDE GLYCOSIDASES HYDROLYZING GINSENOSIDE SUGAR MOIETIES AND USES THEREOF

This application is a national stage entry of PCT/CN00/00744, filed Dec. 29, 2000.

FIELD OF INVENTION

The invention relates to ginsenoside glycosidases which hydrolyze the sugar moieties of the ginsenosides which have higher contents in ginseng to produce rare ginsenosides. The invention also relates to uses of the ginsenoside glycosidases.

BACKGROUND

Ginseng, a famous phytomedicine, has been used as an expensive traditional medicine in oriental countries since ancient times. The main ginseng plants used as medicine are *Panax ginseng* C. A. Meyer, *Panax quinquefolium* L. (American ginseng), *Panax natoginseng* (Sanchi ginseng, or Tienchi ginseng), *Panax japonicus*, and other species of *Panax* genus.

One of the important physiological active ingredients in ginseng plants is saponin (called ginsenoside), and over 30 ginsenosides have been known. Ginsenosides can be categorized in three groups, i.e. protopanaxadiol-type (PPD), protopanaxatriol-type (PPT), and oleanonic acid-type saponins. Ginsenosides $Ra_1$, $Ra_2$, $Ra_3$, $Rb_1$, $Rb_2$, $Rb_3$, Rc, Rd, $F_2$, $Rg_3$, $Rg_5$, $Rh_2$, and $Rh_3$ are protopanaxadiol-type ginsenosides; while Re, $Rg_1$, $Rg_2$, $Rg_4$, $Rh_1$, and $Rh_4$ are protopanaxatriol-type ginsenosides. Ro is an oleanonic acid-type saponin. Ginsenoside $Ra_1$, $Ra_2$, $Ra_3$, $Rb_1$, $Rb_2$, $Rb_3$, Rc, Rd, $F_2$, Re, and $Rg_1$ are dammarane 20(S)-saponins, while ginsenosides $Rg_3$, $Rh_2$, $Rg_2$, and $Rh_1$ have 20(S) and 20(R)-forms. Main ginsenoside structures are as follows:

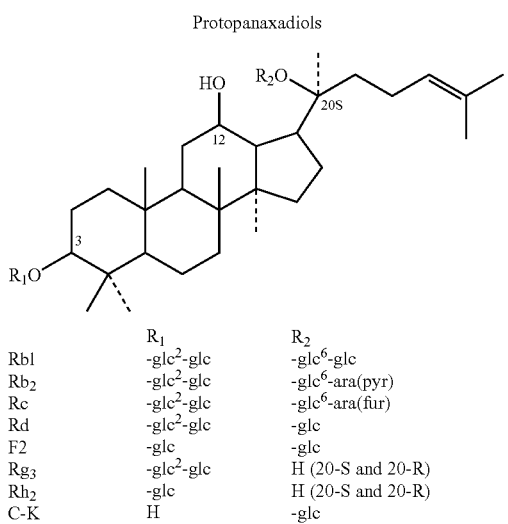

Protopanaxadiols

| | $R_1$ | $R_2$ |
|---|---|---|
| Rb1 | -$glc^2$-glc | -$glc^6$-glc |
| Rb2 | -$glc^2$-glc | -$glc^6$-ara(pyr) |
| Rc | -$glc^2$-glc | -$glc^6$-ara(fur) |
| Rd | -$glc^2$-glc | -glc |
| F2 | -glc | -glc |
| Rg3 | -$glc^2$-glc | H (20-S and 20-R) |
| Rh2 | -glc | H (20-S and 20-R) |
| C-K | H | -glc |

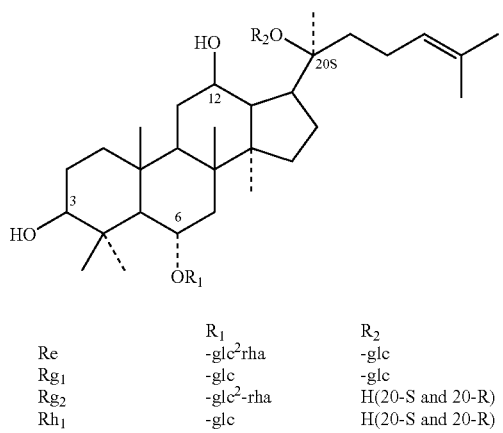

Protopanaxatriols

| | $R_1$ | $R_2$ |
|---|---|---|
| Re | -$glc^2$rha | -glc |
| Rg1 | -glc | -glc |
| Rg2 | -$glc^2$-rha | H(20-S and 20-R) |
| Rh1 | -glc | H(20-S and 20-R) |

Ginsenosides which have higher contents in ginseng are ginsenosides Ra, $Rb_1$, $Rb_2$, Rc, Rd, Re and $Rg_1$, and other ginsenosides such as $Rg_3$, $Rg_2$, $Rg_5$, $Rh_2$, $Rh_1$, $Rh_3$ and $Rh_4$ are rare ginsenosides found only in red ginsengs or wild ginsengs. These rare ginsenosides often have special physiological activities. For example, ginsenosides $Rh_2$, $Rh_3$, $Rg_3$ and $Rh_1$ have good anti-tumor activities with no side effect. Ginsenosides $Rg_3$ and $Rg_2$ have anti-thrombus activities. Therefore, these rare ginsenosides have significant applications in drugs and health foods. However, it is very difficult to obtain rare ginsenosides from red and wild ginsengs because of their low contents in red ginsengs and wild ginsengs.

To obtain rare ginsenosides such as ginsenoside $Rh_2$, chemical synthesis has been tried but the yield was very low (Liu Weicha et al., Journal of Shenyang Medical College 1, 14 (1988)). It has also been suggested to obtain rare ginsenosides by hydrolyzation with alkali or acid (N. Kondo et al., Chem. Pharm. Bull., 21, 2702(1973)). However this method has poor reaction selectivity and low yield. Researchers in Japan have studied the metabolism of ginsenosides in human intestines (M. Kanaoka et al., J. Traditional Medicine, 11, 241(1994)).

So far no satisfactory result has been obtained in the large-scale production of rare ginsenosides, therefore new measures for the large-scale preparation of rare ginsenosides are still needed. The inventors have discovered new enzymes from microorganisms, ginseng plants, wheat brans, almonds, malts, and animal livers which enzymes can hydrolyze the sugar moieties of ginsenosides. Such enzymes, named ginsenoside glycosidase (or ginsenosidase), can hydrolyze ginsenosides Ra, $Rb_1$, $Rb_2$, Rc, Rd, Re and $Rg_1$ which have higher contents in ginsengs, and are thus useful in the large-scale production of rare ginsenosides.

Therefore, it is an object of the invention to provide a new class of enzymes which can hydrolyze the sugar moieties of ginsenosides to prepare rare ginsenosides. The enzymes are designated as ginsenoside glycosidases.

It is another object of the invention to provide various uses of the gensenoside glycosidases of the invention.

SUMMARY OF THE INVENTION

The present invention relates to new enzymes which can hydrolyze the sugar moieties of ginsenosides to produce rare ginsenosides. The enzymes are designated as ginsenoside glycosidases. The enzymes of the invention are obtainable from microorganisms, ginseng plants, wheat brans, almonds, malts and animal livers. The enzymes can be used to hydrolyze ginsenosides with high contents in ginseng plants, such as ginsenosides Ra, $Rb_1$, $Rb_2$, Rc, Rd, Re and $Rg_1$ to obtain rare ginsenosides such as ginsenosides $Rh_1$, $Rh_2$, C-K, $Rg_2$, $Rg_3$, $F_2$, and Rd and aglycone, so as to prepare, in large amount, these and other rare ginsenosides which exist only in red ginsengs and wild ginsengs.

The ginsenoside glycosidases of the invention can be categorized in four groups depending on their enzyme reactions, namely ginsenoside glycosidase I, ginsenoside glycosidase II, ginsenoside glycosidase III and ginsenoside-α-rhamnosidase, in which:

Ginsenoside glycosidase I can hydrolyze the β-glucosidic bonds, β-xylosidic bonds and α-arabinosidic bonds of ginsenosides Ra, $Rb_1$, $Rb_2$, Rc and Rd;

Ginsenoside glycosidase II can hydrolyze the β-glucosidic bonds, β-xylosidic bonds and α-arabinosidic bonds at C-20 (the twentieth carbon atom) of ginsenosides Ra, $Rb_1$, $Rb_2$, Rc and Rd to give ginsenoside Rd;

Ginsenoside glycosidase III can hydrolyze the glycosidic bond between aglycone and sugar moiety at C-3 of ginsenoside Rd to give ginsenoside C-K; and Ginsenoside-α-rhamnosidase can hydrolyze α-rhamnosidic bonds at C-6 of ginsenosides Re and $Rg_2$ to give $Rg_1$ and $Rh_1$, respectively.

One or more of the four ginsenoside glycosidases can be used to hydrolyze ginsenosides with high contents in ginseng plants such as ginsenosides Ra, $Rb_1$, $Rb_2$, Rc, Rd, Re and $Rg_1$ to prepare rare ginsenosides.

The invention further relates to uses of the ginsenoside glycosidases of the invention. For example, the ginsenoside glycosidases of the invention can be used to treat ginsenosides with high contents in ginseng plants and other readily available ginsenosides so as to produce rare and useful ginsenosides. The ginsenoside glycosidases of the invention can also be used to treat total ginsenosides to produce mixed ginsenosides with higher contents of rare ginsenosides. The ginsenoside glycosidases of the invention can also be used to treat ginseng powders to produce ginseng products with higher contents of rare ginsenosides.

The ginsenoside glycosidases of the invention differ from conventional cellulases or hemicellulases in that cellulases or hemicellulases only hydrolyze glucosidic bonds of polysaccharides such as celluloses and semicelluloses, whereas the ginsenoside glycosidases of the invention hydrolyze glucosidic bonds of ginseng dammarane glycosides. For example, β-glucosidase (EC 3.2.1.21) hydrolyzes β-glucosidic bonds of cellulose and cellubiose, but hardly hydrolyzes β-glucosidic bond at C-3 atom of ginsenosides. The reason is that conventional cellulases and hemicellulases hydrolyze glycosidic bond of saccharides, while the ginsenoside glycosidases of the invention hydrolyze glycosidic bonds of glycosides having 30 carbon atoms.

DETAILED DESCRIPTION OF THE INVENTION

After purification and characterization, the ginsenoside glycosidases of the invention were found to have four types, namely, ginsenoside glycosidase I, ginsenoside glycosidase II, ginsenoside glycosidase III and ginsenoside-α-rhamnosidase. Ginsenoside glycosidase I can hydrolyze β-glucosidic bonds, β-xylosidic bonds and α-arabinosidic bonds of ginsenosides Ra, $Rb_1$, $Rb_2$, Rc and Rd. Ginsenoside glycosidase II can hydrolyze β-glucosidic bonds, β-xylosidic bonds and α-arabinosidic bonds at C-20 ($20^{th}$ carbon atom) of ginsenosides Ra, $Rb_1$, $Rb_2$, Rc and Rd to give ginsenoside Rd. Ginsenoside glycosidase III can hydrolyze the glycosidic bond between aglycone and sugar moiety at C-3 of ginsenoside Rd to give ginsenoside C-K. Ginsenoside-α-rhamnosidase can hydrolyze α-rhamnosidic bonds at C-6 of ginsenosides Re and $Rg_2$ to give $Rg_1$ and $Rh_1$, respectively.

The ginsenoside glycosidases of the invention can be used to treat ginsenosides with high contents in ginseng plants and other readily available ginsenosides so as to produce rare and useful ginsenosides. The ginsenoside glycosidases of the invention can also be used to treat total ginsenosides to produce mixed ginsenosides with higher content of rare ginsenosides. The ginsenoside glycosidases of the invention can also be used to treat ginseng powders to produce ginseng products with higher contents of rare ginsenosides.

The ginsenoside glycosidases of the invention may be obtained from microorganism cultures, ginseng plants, wheat brans, almonds, malts and animal livers, etc. The microorganisms comprise bacteria, streptomyces, yeasts, Aspergillus, basidiomycetes, etc. In case of producing the ginsenoside glycosidases with microorganisms, ginseng extracts or ginseng powders may be added to improve the yield of the enzymes. The microorganisms may be cultured in liquid or solid media. In case of culturing in a solid medium, the solid culture medium may be extracted with a buffer and centrifuged to obtain a solution of the enzymes. The liquid culture media may be directly centrifuged to obtain a solution containing the enzymes. In case that ginseng plants or animal livers are used to produce the ginsenoside glycosidases of the invention, these materials may be disrupted, extracted with a buffer and then centrifuged to obtain a solution of the enzymes. For wheat brans, malts and almonds, they may be extracted with a buffer and centrifuged to give a solution containing the enzymes. Optionally, the ginsenoside glycosidases in the solutions thus obtained may further be precipitated by the addition of ammonium sulfate or ethanol, followed by dissolving in a buffer to give a concentrated enzyme solution.

Depending on different sources of the enzymes, the ginsenoside glycosidases of the invention may have different contents of each four above-mentioned types of ginsenoside glycosidases.

The ginsenoside glycosidases of the invention may be used directly to treat ginsenosides to prepare rare ginsenosides. Purified or unpurified enzymes may be used depending on the desired products. Enzyme reactions may be conducted under conditions such as pH 2-11, 5-70° C. and 0.001%-20% ginsenoside substrates. The substrates include protopanaxadiol-type ginsenosides and protopanaxatriol-type ginsenosides. The products from the enzyme reaction are ginsenosides which have partial or complete change of sugar moieties, such as ginsenosides Rh2, Rh1, C-K, Rg2, Rg3, F2, Rg1 and Rd, and their isomers.

The invention will be described in more details with reference to drawings and examples, in which:

FIG. 1 shows the hydrolysis of protopanaxadiol-type ginsenosides by ginsenoside glycosidase I of the invention;

FIG. 2 shows the hydrolysis of protopanaxadiol-type ginsenosides by ginsenoside glycosidase II of the invention;

FIG. 3 shows the hydrolysis of ginsenoside by ginsenoside glycosidase III of the invention; and FIG. 4 shows the hydrolysis of ginsenoside by ginsenoside-α-rhamnosidase of the invention.

FIG. 5 shows the structures of 20(S)- and 20(R)-ginsenosides.

EXAMPLE 1

The Preparation of Ginsenoside Glycosidases from Microorganisms

1. Ginsenosidases from *Aspergillus niger*

The strain used is *Aspergillus niger* FFCCDL-48 g (available from Food Fermentation Culture Collection of Dalian Institute of Light Industry).

1.1 Preparation of the Enzymes

*Aspergillus niger* FFCCDL-48 g was cultured in a medium containing 1% ginseng extracts and 3% wheat bran extracts at 30° C. for 54 hours. Cells were removed by centrifugation, after which $(NH_4)_2SO_4$ powder was added to 2000 ml of the cell-free supernatant with stirring to 65% saturation. The solution was stored overnight at 4° C. and precipitated proteins were collected by centrifugation, resuspended in 80 ml of distilled water and dialyzed against 0.01M acetate buffer pH 5. Insolubles were removed by centrifugation, and the solution was adjusted to 200 ml with 0.01 M acetate buffer pH 5. The crude enzyme solution may be used to hydrolyze ginsenosides or to purify the enzymes.

1.2 Hydrolysis of Ginsenosides 100 mg each of ginsenosides $Rb_1$, $Rb_2$, Rc and Rd and 10 mg of ginsenoside $Rg_3$ were dissolved in separate tubes containing 10 ml of 0.01M acetate buffer pH 5. 10 ml of the crude enzyme solution obtained in 1.1 was added to each tube and allowed to react at 30° C. for 18 hours. Then 10 ml of n-butanol was added to stop the reactions. The products were measured by thin layer chromatography (TLC) (Silica gel 60-F254, Merck; chloroform:methanol:water 70:30:5). Table 1 shows the results detected by Shimadzu TLC Scanner CS-930.

TABLE 1

Hydrolysis of various protopanaxadiol-type ginsenosides with the ginsenoside glycosidases from *A. niger*

| | Percentage of ginsenosides in the reaction product(%) | | | | | | | |
|---|---|---|---|---|---|---|---|---|
| Substrate | $Rb_1$ | $Rb_2$ | Rc | Rd | $Rg_3$ | $F_2$ | $Rh_2$ | C—K | aglycone |
| $Rb_1$ | 1 | | | 10 | | 63 | 5 | 16 | 5 |
| $Rb_2$ | | 7 | | 13 | | 57 | 3 | 17 | 3 |
| Rc | | | 8 | 12 | | 58 | 2 | 15 | 5 |
| Rd | | | | 15 | | 50 | 5 | 25 | 5 |
| $Rg_3$ | | | | | 30 | | 53 | 17 | |

The reactions were carried out at pH 5, 30° C. for 18 hours. The hydrolysis results of ginsenosides $Ra_1$, $Ra_2$ and $Ra_3$ (data not shown) were similar to those of $Rb_1$.

It was shown in Table 1 that the enzymes from *A. niger* can hydrolyze the sugar-moieties of protopanaxadiol-type ginsenosides with a conversion rate of more than 90%. The conversion rate from $Rg_3$ to Rh2 is over 50%. The main products of the enzyme reactions were ginsenosides $F_2$, C-K, Rh2 and aglycone. The hydrolysis of ginsenosides $Ra_1$, $Ra_2$ and $Ra_3$ with the ginsenoside glycosidases from *A. niger* is similar to the hydrolysis of $Rb_1$.

It can be drawn from the above-mentioned experiments that the ginsenoside glycosidases from *A. niger* at least have the activities of hydrolyzing C-3 β-(1→2)-D-glucoside, C-20 β-(1→6)-D-glucoside, C-20 α-(1→6)-L-arabinoside and C-20 β-(1→6)-D-xyloside.

The production of the ginsenoside glycosidases is induced by the addition of ginseng extracts or ginsenosides. That is, the yield of the enzymes increases when ginseng extracts or ginsenosides are added in the culture medium and the yield decreases if these inducers are not added.

1.3 Properties of the Ginsenoside Glycosidases from *A. niger*

Experiments were carried out to explore the effects of temperature, pH, metal ions and reaction time on the enzyme reaction, in order to further characterize the enzymes.

Effect of temperature on the enzyme reaction:

100 mg of ginsenoside $Rb_1$ was used in a reaction under the conditions as described in 1.2 and the effect of temperature was shown in Table 2.

TABLE 2

Temperature effect on the hydrolysis of ginsenoside $Rb_1$ with the enzymes from *A. niger*

| Temperature (° C.) | Percentage of ginsenosides in the reaction product (%) | | | | | | |
|---|---|---|---|---|---|---|---|
| | $Rb_1$ | Rd | $Rg_3$ | $F_2$ | $Rh_2$ | C—K | aglycone |
| 20 | 25 | 50 | — | 15 | — | 10 | — |
| 30 | 1 | 10 | — | 63 | 5 | 16 | 5 |
| 40 | — | 5 | — | 50 | 6 | 34 | 5 |
| 50 | — | 5 | — | 40 | 4 | 42 | 4 |
| 60 | 30 | 50 | — | 10 | 2 | 6 | 2 |
| 70 | 82 | 18 | — | — | — | — | — |

The reaction was carried out at pH 5.0, 30° C. for 18 hours and the concentration of $Rb_1$ was 0.5%.

As shown in Table 2, Rb, is hydrolyzed better under a temperature range of 30 to 60° C. The yields of ginsenosides $F_2$ and C-K are higher under a temperature range of 20 to 50° C. Under 20 to 50° C., the yield of ginsenoside C-K increases with the increase of temperature. It can be drawn from Table 2 that the temperature is preferably kept in the range of 30 to 40° C. if more ginsenoside $F_2$ is desired, while the temperature is preferably kept in the range of 40-50° C. if more ginsenoside C-K is desired. More ginsenoside Rd may be obtained if the reaction is carried out in a temperature of 20° C. or 60° C. The yields of ginsenosides $Rg_3$ and Rh2 and aglycone are relatively lower. The temperature effects on the hydrolysis of Ra, $Rb_2$, Rc and Rd are similar to the effect on $Rb_1$.

Effect of pH on the enzyme reaction:

The effect of different pH on the enzyme reaction was shown in Table 3.

TABLE 3 pH effect on the hydrolysis of ginsenoside $Rb_1$ with the enzymes from *A. niger*

| pH | Percentage of ginsenosides in the reaction product (%) | | | | | | |
|---|---|---|---|---|---|---|---|
| | $Rb_1$ | Rd | $Rg_3$ | $F_2$ | $Rh_2$ | C—K | aglycone |
| 3.0 | 2 | 20 | — | 30 | 8 | 40 | 10 |
| 4.0 | 1 | 10 | — | 43 | 7 | 39 | 5 |
| 5.0 | — | 10 | — | 63 | 5 | 16 | 5 |
| 6.0 | — | 15 | — | 56 | 4 | 21 | 4 |
| 7.0 | 10 | 41 | 2 | 41 | 2 | 6 | 2 |
| 8.0 | 20 | 45 | 3 | 36 | — | 6 | — |

The reaction was carried out at 30° C. for 18 hours and the concentration of $Rb_1$ was 0.5%.

As shown in Table 3, the yield of ginsenosides $F_2$ is higher at pH 4 to 7 and the yields of ginsenosides C-K and Rh2 and aglycone increase with the increase of pH. The pH effects on the hydrolysis of Ra, $Rb_2$, Rc and Rd are similar to the effect on $Rb_1$.

Effect of reaction time on the enzyme reaction:

The effect of different reaction time on the enzyme reaction was shown in Table 4.

TABLE 4

The effect of reaction time on the hydrolysis of ginsenoside $Rb_1$ with the enzymes from *A. niger*

| Reaction time | Percentage of ginsenosides in the reaction product (%) | | | | | | |
|---|---|---|---|---|---|---|---|
| (hours) | $Rb_1$ | Rd | $Rg_3$ | $F_2$ | $Rh_2$ | C—K | aglycone |
| 1  | 38 | 62 | — | —  | — | —  | — |
| 4  | 12 | 72 | — | 10 | — | —  | — |
| 8  | 8  | 51 | — | 38 | — | 2  | — |
| 12 | 6  | 30 | — | 54 | 2 | 6  | 2 |
| 18 | —  | 10 | — | 63 | 5 | 16 | 5 |
| 24 | —  | 8  | — | 60 | 4 | 24 | 4 |
| 30 | —  | 5  | 2 | 40 | 6 | 44 | 3 |
| 36 | —  | 2  | 3 | 30 | 7 | 52 | 6 |

The reaction was carried out at pH 5, 30° C. and the concentration of $Rb_1$ was 0.5%.

As shown in Table 4, at beginning the glucoside at C-20 of ginsenoside $Rb_1$ is hydrolyzed to yield Rd. The yield of Rd decreases with the reaction time, whereas the contents of $F_2$ and C-K increase. The yield of F2 is the highest when the reaction lasts for 12 to 24 hours. The yields of ginsenosides C-K and $Rh_2$ and aglycone increase with the reaction time.

The effects of reaction time on the hydrolysis of Ra, $Rb_2$, Rc and Rd are similar to the effect on $Rb_1$.

Effects of metal ions:

The effect of metal ions on the enzyme reaction was shown in Table 5

TABLE 5

The effect of metal ions on the hydrolysis of ginsenoside $Rb_1$ with the enzymes from *A. niger*

| Metal ions | | Percentage of ginsenosides in the reaction product (%) | | | | | |
|---|---|---|---|---|---|---|---|
| (mM) | | $Rb_1$ | Rd | $Rg_3$ | $F_2$ | $Rh_2$ | C—K | aglycone |
| No ion |     | — | 10 | — | 63 | 5 | 16 | 2 |
| $Ca^{++}$ | 50  | — | 4  | — | 65 | 7 | 20 | 4 |
|           | 100 | — | —  | — | 67 | 7 | 21 | 5 |
| $Mg^{++}$ | 50  | — | 6  | — | 65 | 7 | 17 | 5 |
|           | 100 | — | —  | — | 67 | 8 | 21 | 4 |

TABLE 5-continued

The effect of metal ions on the hydrolysis of ginsenoside $Rb_1$ with the enzymes from *A. niger*

| Metal ions | | Percentage of ginsenosides in the reaction product (%) | | | | | |
|---|---|---|---|---|---|---|---|
| (mM) | | $Rb_1$ | Rd | $Rg_3$ | $F_2$ | $Rh_2$ | C—K | aglycone |
| $Cu^{++}$ | 100 | 30 | 30 | — | 30 | — | 10 | — |
| $Pb^{++}$ | 100 | 70 | 20 | — | 9  | — | 1  | — |

The reaction was carried out at pH 5.0, 30°C. and the concentration of $Rb_1$ was 0.5%.

As shown in Table 5, $Ca^{++}$ and $Mg^{++}$ can slightly accelerate the conversion rate, whereas $Cu^{++}$ and $Pb^{++}$ inhibit the reaction. The effects of metal ions on the hydrolysis of Ra, $Rb_2$, Rc and Rd are similar to the effect on $Rb_1$.

1.4 Purification of the Ginsenoside Glycosidases from *A. niger*

10 ml of the enzyme solution obtained in 1.1 was subjected to a DEAE-Cellulose DE-52 column (Pharamcia, 1.5×6.7 cm) to absorb the enzyme protein. The column was then eluted with a NaCl gradient (0.06, 0.12, 0.18, 0.24, 0.3, 0.4, 0.5 and 0.6M).

Fractions 36 and 54 from the DEAE-Cellulose column appeared as one dot on a SDS-polyacrylamide gel, representing the purified enzymes. The hydrolysis of ginsenosides with the purified enzymes was shown in Table 6.

TABLE 6

The hydrolysis of ginsenosides with Fraction 36 (ginsenoside glycosidase I)

| Substrate | Percentage of ginsenosides in the reaction product (%) | | | | | | | | | |
|---|---|---|---|---|---|---|---|---|---|---|
|  | $Rb_1$ | $Rb_2$ | Rc | Rd | $Rg_3$ | $Rg_2$ | $F_2$ | $Rh_2$ | $Rh_1$ | C—K | Aglycone |
| $Rb_1$ | — |   |   | 8 |   |   | 38 | 1 |   | 49 | 2 |
| $Rb_2$ |   | — |   | 9 |   |   | 35 | 1 |   | 54 | 1 |
| Rc     |   |   | — | 8 |   |   | 36 | 2 |   | 52 | 2 |
| Rd     |   |   |   |   |   |   | 50 |   |   | 25 | 5 |
| $Rg_3$ |   |   |   |   | 40 |  |    | 57 |   |    | 3 |
| $F_2$  |   |   |   |   |   |   | 30 | 3 |   | 62 | 5 |
| $Rh_2$ |   |   |   |   |   |   |    | 89 |   |    | 10 |
| C—K    |   |   |   |   |   |   |    |    |   | 97 | 3 |
| $Rg_2$ |   |   |   |   |   | 100 |  |    |   |    |   |

Concentrations of substrates $Rb_1$, $Rb_2$, Rc and Rd: 0.5%; $Rg_3$, $F_2$, $Rh_2$, C—K and $Rg_2$: 0.05%. The reaction was carried out at pH 5.0, 30° C. The hydrolysis of ginsenosides Ra was similar to that of $Rb_1$.

Fraction 36 which was eluted with 0.12 M NaCl from the DEAE-Cellulose column was lyophilized and appeared as a single dot with a molecular weight of 51,000 Daltons when running on a SDS-polyacrylamide gel. Therefore, it represented a purified enzyme and designated as ginsenoside glycosidase I whose properties were shown in Table 6.

It can be seen from Table 6 that Fraction 36 (ginsenoside glycosidase I) can hydrolyze β-(1→6)-D-glucoside at C-20 of $Rb_1$, α-(1→6)-L-arabinoside at C-20 of Rc and $Rb_2$ and β-(1→6)-D-xyloside at C-20 of Ra ginsenosides. It can also hydrolyze β-(1→2)-D-glucoside at C-3 of protopanaxadiol-type ginsenosides such as Ra, $Rb_1$, $Rb_2$, Rc, Rd and $Rg_3$ and slightly hydrolyze β-D-glucosyl at C-3 and β-glucosyl at C-20 of aglycone. The hydrolysis mechanism of ginsenoside glycosidase I is shown in FIG. 1. Ginsenoside glycosidase I also hydrolyzes β-glucoside, β-xyloside, α-arabinoside, β-galactoside, but not p-nitrophenyl-α-rhamnoside.

Ginsenoside Glycosidase II

Fraction 54 which was eluted with 0.18 M NaCl from the DEAE-Cellulose column was lyophilized and appeared as a single dot when running on a SDS-polyacrylamide gel with a molecular weight of 90,000 Daltons. Therefore, it represented a purified enzyme and designated as ginsenoside glycosidase II. This enzyme only hydrolyzes β-(1→6)-D-glucoside at C-20 of $Rb_1$, β-(1→6)-D-xyloside of Ra ginsenosides and α-(1→6)-L-arabinoside at C-20 of Rc and $Rb_2$ to give Rd, slightly hydrolyzes Rd to give $Rg_3$, but does not hydrolyze β-(1→2)-D-glucoside at C-3 of protopanaxadiol-type ginsenosides. The hydrolysis mechanism of ginsenoside glycosidase II is shown in FIG. 2.

Ginsenoside glycosidase II was purified from the crude enzyme solution obtained in 1.1 by HPLC. Separation column: Bio-Scale Q (BioRad), 2 ml/tube. 1 ml of the crude enzyme solution was loaded on the column, and eluted with solvent A (25 mM Tris-HCl buffer pH 7.4) and solvent B (0.5M NaCl in 20 mM Tris-HCl buffer pH 7.4). Fraction 18 appeared as a single dot when running on a SDS-polyacrylamide gel and thus represented a purified enzyme. The enzyme was designated as ginsenoside glycosidase III. This enzyme can hydrolyze the diglucosyl groups at C-3 of aglycone, converting Rd and $Rg_3$ to C-K and aglycone. The hydrolysis mechanism of ginsenoside glycosidase II is shown in FIG. 3.

In summary, the properties of the above three ginsenoside glycosidases from *A. niger* are shown in Table 7.

Cellulose β-glucosidases (EC 3.2.1.21) from *Clostridium thermocopiriae* and *Bacillus* sp. AX cannot hydrolyze any glycosides of ginsenosides. The cellulose β-glucosidase from almond slightly hydrolyzes the C-20 glycoside of $Rb_1$, $Rb_2$ and Rc to give ginsenoside Rd, but it cannot hydrolyze the glucoside at C-3. Ginsenoside glycosidase II is similar to cellulose β-glucosidase from almond, but it only slightly hydrolyzes Rd. The properties of ginsenoside glycosidase III are totally different from those of cellulose β-glucosidases.

An exo-cellulase from *Clostridium thermocopiriae* (cellobiose-producing enzyme) cleaves cellodextrin to give cellobiose, but cannot hydrolyze diglucosidic bond at C-3 of ginsenoside Rd. So it is completely different from ginsenoside glycosidase III. Therefore, the ginsenoside glycosidases of the invention are enzymes different from known cellulose β-glucosidases and cellobiose-producing enzymes.

2. Ginsenoside Glycosidases from *Aspergillus oryzae*

2.1 The Preparation of the Enzymes

*Aspergillus oryzae* FFCCDL-39 g (available from Food Fermentation Culture Collection of Dalian Institute of Light

TABLE 7

Properties of the above three ginsenoside glycosidases from *A. niger*

| | Optimal temp. (° C.) | Optimal pH | MW | Hydrolyzing glycosidic bonds |
|---|---|---|---|---|
| ginsenoside glycosidase I | 30-40 | 4-6 | 51,000 | C-20 β-glucoside, β-xyloside, and α-arabinoside C-3 glucoside |
| ginsenoside glycosidase II | 30-40 | 5-7 | 90,000 | C-20 β-glucoside, β-xyloside, and α-arabinoside |
| ginsenoside glycosidase III | 30-45 | 4-5 | 34,000 | C-3 β-diglucoside |

1.5 Differences Between Ginsenoside Glycosidases and Cellulose β-Glucosidase

To observe the differences between the ginsenoside glycosidases of the invention and known exo-cellulases, the ginsenoside glycosidases of the invention were compared with cellulose β-glucosidase (E.C. 3.2.1.21) in two reactions with 0.5% ginsenosides $Rb_1$ or Rd as substrate. The reaction was carried out at pH 5.0, 30° C. for 18 hours and the results were shown in Table 8.

Industry) was cultured with stirring in a medium containing 1% ginseng extracts and 3% wheat bran extracts at 30° C. for 64 hours. Cells were removed by centrifugation, after which $(NH_4)_2SO_4$ powder was added to 2000 ml of the cell-free supernatant with stirring to 65% saturation. The solution was stored overnight at 4° C. and precipitated proteins were collected by centrifugation, resuspended in 80 ml of distilled water and dialyzed against 0.01M acetate buffer pH 5. Insolubles were removed by centrifugation, and the solution

TABLE 8

Comparison of ginsenoside glycosidases and other similar enzymes

| | | Percentage of ginsenosides in the reaction product (%) | | | | | | | | |
|---|---|---|---|---|---|---|---|---|---|---|
| Enzymes | Substrates | $Rb_1$ | Rd | $Rg_3$ | $Rg_2$ | $F_2$ | $Rh_2$ | $Rh_1$ | C—K | Aglycone |
| ginsenoside glycosidase I | $Rb_1$ | — | 8 | | | 38 | 1 | | 49 | 2 |
| | Rd | | | | | 50 | | | 25 | 5 |
| ginsenoside glycosidase II | $Rb_1$ | — | 90 | 5 | | | | | | |
| | Rd | | 90 | 5 | | | | | | |
| ginsenoside glycosidase III | Rd | | 61 | | | | | | 36 | 3 |
| Almond cellulose β-glucosidase(EC 3.2.1.21) | $Rb_1$ | 80 | 20 | | | | | | | |
| | Rd | 100 | — | | | — | | | | |
| Cellulose β-glucosidase of Clostridium and Bacillus (EC 3.2.1.21) | $Rb_1$ | 100 | — | | | — | | | | |
| | Rd | 100 | — | | | — | | | | |
| Cellobiose-producing enzyme from Clostridium | $Rb_1$ | 100 | — | | | — | | | | |
| | Rd | 100 | — | | | — | | | | |

Concentrations of $Rb_1$ and Rd: 0.5%; pH 5.0, 30° C. for 18 hours.

was adjusted to 200 ml with 0.01 M acetate buffer pH 5. The crude enzyme solution may be used to hydrolyze ginsenosides or to purify the enzymes.

Each 100 mg of ginsenosides $Rb_1$, $Rb_2$, Rc Re and Rd and each 10 mg of ginsenoside $Rg_3$ and $Rg_2$ were dissolved in separate tubes containing 10 ml of 0.01M acetate buffer pH 5. 10 ml of the crude enzyme solution obtained as above was added to each tube and allowed to react at 30° C. for 18 hours. Then 10 ml of n-butanol was added to stop the reactions. The products were measured by thin layer chromatography (TLC) (Silica gel 60-F254, Merck; chloroform:methanol:water 70:30:5). Table 9 shows the results detected by Shimadzu TLC Scanner CS-930.

TABLE 9

Hydrolysis of various ginsenosides with the ginsenoside glycosidases from *A. oryzae*

Percentage of ginsenosides in the reaction product(%)

| substrate | $Rb_1$ | $Rb_2$ | Rc | Rd | Re | $Rg_3$ | $Rg_2$ | $Rg_1$ | $F_2$ | $Rh_2$ | $Rh_1$ | C—K | aglycone |
|---|---|---|---|---|---|---|---|---|---|---|---|---|---|
| $Rb_1$ | — | | | 20 | | | | | 38 | | | 45 | 2 |
| $Rb_2$ | | — | | 18 | | | | | 35 | | | 54 | 3 |
| Rc | | | — | 19 | | | | | 30 | | | 56 | 5 |
| Rd | | | | 25 | | 1 | | | 40 | | | 29 | 5 |
| $Rg_3$ | | | | | | 45 | | | | 50 | | | 5 |
| Re | | | | | 20 | | | 73 | | | 2 | | 5 |
| $Rg_2$ | | | | | | | 32 | | | | 75 | | 3 |

The reactions were carried out at pH 5.0, 30° C. for 18 hours.

It can be seen from Table 9 that the properties of the ginsenoside glycosidases from *A. oryzae* in terms of hydrolyzing protopanaxadiol-type ginsenoside, such as the effects of pH, temperature and reaction time are all similar to those of the ginsenoside glycosidases from *A. niger*. The only difference is that the enzymes from *A. niger* cannot hydrolyze α-(1→2)-L-rhamnosidic bond at C-6 of ginsenosides Re and $Rg_2$, however, the ginsenoside glycosidases from *A. oryzae* can hydrolyze the same to give $Rg_1$ and $Rh_1$. This demonstrates that the ginsenoside glycosidases from *A. oryzae* also have the activity of ginsenoside-α-(1→2)-L-rhamnosidase (i.e. ginsenoside-α-rhamnosidase) in addition to the activities of ginsenoside glycosidases I, II, and III.

2.2 Purification and Characterization of Ginsenoside-α-Rhamnosidase

To investigate the properties of the ginsenoside-α-L-rhamnosidase from *A. oryzae*, the enzyme was purified with Biologic Medium Pressure Chromatography (BioRad). The parameters were as following: column, Bio-Scale Q2 (Bio-Rad); crude enzyme, 1 ml; flow rate, 1 ml/minute; mobile phase, 25 mM Tris-HCl pH 8.2 and 0.5M NaCl in 25 mM Tris-HCl pH 8.2; 2 ml/tube.

The activities of each fraction were tested and fraction 16 was found to have ginsenoside-α-rhamnosidase activities. The ginsenoside-α-L-rhamnosidase appeared as a single dot with a molecular weight of 53,000 when running on a SDS-polyacrylamide gel, indicating that the enzyme of fraction 16 was a purified enzyme.

The purified ginsenoside-α-rhamnosidase can hydrolyze the α-L-rhamnoside at C-6 of ginsenosides Re and $Rg_2$ to produce $Rg_1$ and $Rh_1$, respectively. The enzyme is more active at pH 4 to 7 (with an optimal pH of 5), 30 to 50° C. (with an optimal temperature of 40° C.). Purified ginsenoside-α-rhamnosidase only hydrolyzes α-L-rhamnoside at C-6 of protopanaxatriol-type ginsenosides, but does not hydrolyze any other glycosidic bonds of ginsenosides. The mechanism for the hydrolysis of Re and $Rg_2$ with ginsenoside-α-rhamnosidase is shown in FIG. 4.

3. Ginsenoside Glycosidases from Bacteria

Thermophilic and aerobic Bacillus sp. JF (Fengxie Jin et al., J. Gen. Appl. Microbiol., 36, 415-434, 1990) was cultured with aeration and stirring in a medium containing 0.5% by weight of ginseng extracts, 1% by weight of wheat bran extracts and 0.3% tryptone with a pH of 7.2 at 60° C. for 36 hours. Cells were removed by centrifugation and 3000 ml of 95% ethanol was added to 1000 ml of the cell-free supernatant. The solution was allowed to stand at 4° C. overnight and then centrifuged to collect the pellets. The enzyme protein pellets were dissolved in 50 ml of 0.01M acetate buffer pH 5. Insoluble materials were removed by centrifugation and a crude enzyme solution was obtained.

10 ml of the enzyme solution was allowed to react with 10 ml of 0.5% Rd in acetate buffer containing 20% ethanol at 70° C. for 16 hours. TLC detection showed that 60% of Rd was converted to ginsenoside $F_2$, indicating that bacterial ginsenoside glycosidases can hydrolyze β-(1→2)-glucoside at the third carbon atom of Rd. The enzymes can also hydrolyze β-(1→2)-glucoside of $Rg_3$ to give $Rh_2$.

The optimal reaction temperature for the enzymes is 70° C. and the optimal pH is pH 6.0.

4. Ginsenoside Glycosidases from Yeast

Candida sp. FFCCDL-2 g (available from Food Fermentation Culture Collection of Dalian Institute of Light Industry) was cultured with shaking at 30° C. for 56 hours in a medium containing 2% by weight of ginseng extracts and 8% by weight of malt extracts. Cells were removed by centrifugation, after which $(NH_4)_2SO_4$ powder was added to 500 ml of the cell-free supernatant to 65% saturation. The solution was dialyzed against 0.01M acetate buffer pH 5. Insolubles were removed by centrifugation, and 25 ml of crude enzyme solution was obtained.

10 ml of the enzyme solution was allowed to react with 10 ml of 0.5% Rd in acetate buffer at 60° C. for 12 hours. TLC detection showed that 73% of Rd was converted to ginsenoside $F_2$, indicating that the enzymes can hydrolyze β-(1→2)-glucoside on the third carbon atom of Rd. The enzymes can also hydrolyze β-(1→2)-glucoside of $Rg_3$ to give $Rh_2$.

The optimal reaction temperature for the enzymes is 45° C. and the optimal pH is pH 5.5.

5. Ginsenoside Glycosidases from *Streptomyces*

*Streptomyces* sp. FFCCDL-2 g (available from Food Fermentation Culture Collection of Dalian Institute of Light Industry) was cultured at 30° C. for 48 hours in a medium containing 1% by weight of ginseng extracts and 3% by weight of wheat bran extracts. Cells were removed by centrifugation, after which $(NH_4)_2SO_4$ powder was added to 300 ml of the cell-free supernatant to 70% saturation to precipitate the enzymes. The solution was stored at 4° C. overnight and centrifuged to collect the pellets. The pellets were resuspended and the suspension was dialyzed against 0.01M acetate buffer pH 5. Impurities were removed by centrifugation, and 15 ml of crude enzyme solution was obtained.

10 ml of the enzyme solution was allowed to react with 10 ml of 1% Rd in acetate buffer containing 20% ethanol at 50° C. for 20 hours. TLC detection showed that 50% of Rd was converted to ginsenoside $F_2$, indicating that the ginsenoside glycosidases from *Streptomyces* can hydrolyze β-(1→2)-glucoside at the third carbon atom of Rd.

The optimal reaction temperature for the enzymes is 50° C. and the optimal pH is pH 5.5.

5. Ginsenoside Glycosidases from Basidiomycetes

*Tremella* sp. FFCCDL-12 g (available from Food Fermentation Culture Collection of Dalian Institute of Light Industry) was cultured on a solid medium containing 125 g of ginseng powder, 374 g of wheat bran and 500 ml of water for 5 to 7 days. Then 2500 ml of 0.01 M acetate buffer pH 5.0 was added to the solid medium to stand for 2 hours. Insolubles were removed by centrifugation and approximately 2000 ml liquid was obtained. $(NH_4)_2SO_4$ powder was added to the liquid with stirring to 70% saturation. The solution was stored at 4° C. overnight and centrifuged to collect the pellets. The pellets were resuspended and the suspension was dialyzed against 0.01M acetate buffer pH 5. Then the solution was diluted in 0.01 M acetate buffer to a volume of 150 ml. Impurities were removed by centrifugation, and crude enzyme solution was obtained.

10 ml of the enzyme solution was allowed to react with 10 ml of 1% $Rb_1$ in acetate buffer containing 20% ethanol at 40° C. for 20 hours. TLC detection showed that $Rb_1$ was converted to a mixture of 25% Rd, 40% $F_2$ and 35% C-K. This result indicates that the ginsenoside glycosidases from *Tremella* can hydrolyze β-glucoside on the third carbon atom, and glucoside on the twentieth carbon atom. The optimal reaction temperature for the enzymes is 50° C. and the optimal pH is pH 5.5.

From the above-mentioned experiments, it can be concluded that microorganisms such as bacteria, streptomyces, yeasts, molds and basidiomycetes can produce ginsenoside glycosidases and the yield of the enzymes may be increased when the microorganisms are cultured in a medium containing ginseng extracts. The ginsenoside glycosidases of the invention are different from conventional cellulases (such as cellulose β-glucosidase (EC 3.2.1.21) and cellobiose-producing enzyme) in terms of reaction properties. The ginsenoside glycosidases of the invention can be categorized to four types depending on their capability of hydrolyzing ginsenosides, i.e. ginsenoside glycosidase I, ginsenoside glycosidase II, ginsenoside glycosidase III and ginsenoside-α-rhamnosidase.

EXAMPLE 2

Ginsenoside Glycosidases from Ginseng Plants 2.1 Extraction and Purification of the Enzymes 200 g of fresh ginseng root was cut into pieces and added to 600 ml of 0.02 M acetate buffer pH 5. Supernatant was obtained by filtration after the mixture stand at 40° C. for 2 hours. To the supernatant $(NH_4)_2SO_4$ was added gradually until 70% saturation and the mixture stand overnight at 4° C. Then protein pellets were collected by centrifugation and redissolved in 15 ml of distilled water. The solution was dialyzed against 0.02 M Tris-HCl pH 7.4. Insolubles were removed by centrifugation and the volume of the supernatant was adjusted to 20 ml.

5 ml of the enzyme solution was subjected to a DEAE-Cellulose DE-25 column (Whatman, 1.4×6.7 cm). The column was eluted with a KCl gradient (0.06, 0.12, 0.18 and 0.24 M) in 0.02 M Tris-HCl pH 7.4. After elution, each fraction was tested for the activity of hydrolyzing ginsenosides. Fraction 37 was found to hydrolyze the glucosidic bond between the diglucose at C-3 and aglycone, converting Rd to C-K. Fraction 52 was found to hydrolyze the β-(1→2)-glucoside at the third carbon atom of Rd, resulting $F_2$. Fraction 52 can also hydrolyze the glucosidic bond at the twentieth carbon atom of Rb and Rc to give ginsenoside $F_2$. The results were shown in Table 10.

TABLE 10

Hydrolysis of ginsenosides by the ginsenoside glycosidases from ginseng plant

| | | Percentage of ginsinosides in the reaction product (%) | | | | | |
|---|---|---|---|---|---|---|---|
| Fraction | Substrate | Rd | $Rg_3$ | $F_2$ | C—K | $Rh_2$ | aglycone |
| 52 | $Rb_1$ | 30 | | 70 | | | |
| | $Rb_2$ | 35 | | 65 | | | |
| | Rc | 45 | | 55 | | | |
| | Rd | 60 | | 40 | | | |
| 37 | Rd | 45 | | | 55 | | |

Substrate concentration: 0.5%; the reaction was carried out at 50° C., pH 5.0 for 18 hours.

It can be seen from Table 10, fraction 52 eluted from DEAE-Cellulose column can hydrolyze the glucosidic bond on the twentieth carbon atom of ginsenosides $Rb_1$, $Rb_2$ and Rc, and the β-(1→2)-glucoside on the third carbon atom. Fraction 52 appeared as a single dot when running on a SDS-polyacrylamide gel, and the molecular weight of the enzyme was calculated as 59,000. Therefore the enzyme in fraction 52 is ginsenoside glycosidase I. However, compared with the ginsenoside glycosidase I from *A. niger*, the ginsenoside glycosidase I from ginseng plants has a slightly larger molecular weight and cannot hydrolyze the glycosidic bond directly associated with aglycone. Purified enzyme from fraction 37 can hydrolyze the glucosidic bond between the diglucose at the third carbon atom and aglycone to give ginsenoside C-K, so this enzyme is categorized as ginsenoside glycosidase III.

Calcium ion has an enhancing effect to both enzymes, whereas copper ion has an inhibitory effect. The properties of the purified enzymes are summarized in Table 11.

TABLE 11

Properties of the two ginsenoside glycosidases purified from ginseng plant

| Enzyme | Optimal temperature (° C.) | Optimal pH | M.W. | Fraction # |
|---|---|---|---|---|
| Ginsenoside glycosidase I | 60 | 4-6 | 59,000 | 52 |
| Ginsenoside glycosidase III | 45-55 | 4-5 | 36,000 | 37 |

EXAMPLE 3

Ginsenoside Glycosidases from Wheat Bran

3.1 Extraction of the Enzymes 500 g of wheat bran was added to 2500 ml of 0.02 M acetate buffer pH 5 and extracted at 40° C. for 2 hours. 2000 ml of supernatant were obtained by filtration to which $(NH_4)_2SO_4$ was added gradually with stirring until 70% saturation. The mixture stand at 4° C. overnight. Protein pellets were collected by centrifugation and redissolved in 80 ml of distilled water and dialyzed against 0.02 M acetate buffer pH 5.0. Insolubles were removed by centrifugation and the supernatant was adjusted to a volume of 200 ml to obtain the crude enzyme solution.

3.2 The Properties of the Enzyme 10 ml of the enzyme solution was allowed to react with 10 ml of 1% ginsenoside substrate at 40° C. for 20 hours. The product was detected by TLC and the results were shown in Table 12.

TABLE 12

Hydrolysis of ginsenosides with ginsenoside glycosidases from wheat bran

| substrate | Percentage of ginsenosides in the reaction product (%) | | | | | |
|---|---|---|---|---|---|---|
| | Rd | $Rg_3$ | $F_2$ | C—K | $Rh_2$ | aglycone |
| $Rb_1$ | 40 | | 55 | | | |
| $Rb_2$ | 45 | | 50 | | | |
| Rc | 43 | | 55 | | | |
| Rd | 60 | | 40 | | | |

It can be seen from Table 12, that the enzymes from wheat bran can hydrolyze the glucoside at the third carbon atom of Rd to give $F_2$, and the glycosides at the twentieth and third carbon atoms of $Rb_1$, $Rb_2$ and Rc to give $F_2$.

The optimal pH for the enzymes is 5.0 and the optimal temperature is 40° C. $Fe^{++}$ and $Mg^{++}$ may enhance the enzyme activity, whereas $Cu^{++}$ has an inhibitory effect.

EXAMPLE 4

Ginsenoside Glycosidases from Other Resources

4.1 Enzymes from Malts 200 g of malt was ground and added to 1000 ml of 0.01 M acetate buffer pH 5 for extraction under room temperature for two hours. The mixture was filtrated. To the supernatant 3 volumes of ethanol was added and stand overnight. Precipitates were collected to which 50 ml of 0.01 M acetate buffer pH 5 was added. Insolubles were removed and enzyme solution was obtained. 10 ml of the enzyme solution was allowed to react with 10 ml of 1% $Rb_1$ solution (in 0.01 M acetate buffer pH 5 containing 20% ethanol) at 40° C. for 20 hours. The product was detected by TLC. As a result, more than 95% $Rb_1$ was converted to Rd, $F_2$, C-K and $Rg_3$ and the like. These data demonstrate that the enzymes can hydrolyze the β-glucoside at the third carbon atom of ginsenosides as well as the glycosides at the twentieth carbon atom.

4.2 Enzymes from Animal Liver 100 g of bovine liver was minced and added to 300 ml of 0.01 M acetate buffer pH 5 for extraction under room temperature for two hours. The mixture was centrifuged and $(NH_4)_2SO_4$ was added to the supernatant to 70% saturation to precipitate the enzymes. The mixture was stored at 4° C. overnight. Precipitates were collected by centrifugation and dialyzed against 0.01 M acetate buffer pH 5. Impurities were removed and 15 ml of enzyme solution was obtained. 10 ml of the enzyme solution was allowed to react with 10 ml of 1% $Rb_1$ solution (in 0.01 M acetate buffer pH 5 containing 20% ethanol) at 40° C. for 20 hours. TLC detection showed that 50% of $Rb_1$ was converted to ginsenosides with lower sugar contents, indicating that there are ginsenoside glycosidases in animal liver.

4.3 Enzymes from Plant Seeds—Almond 100 g of almond was ground and added to 300 ml of 0.01 M acetate buffer pH 5 for extraction under room temperature for two hours. The mixture was centrifuged. $(NH_4)_2SO_4$ was added to the supernatant to 60% saturation to precipitate the enzymes. The mixture was stored at 4° C. overnight. Precipitates were collected by centrifugation and dialyzed against 0.01 M acetate buffer pH 5. Impurities were removed and 30 ml of enzyme solution was obtained. 10 ml of the enzyme solution was allowed to react with 10 ml of 1% $Rb_1$ solution (in 0.01 M acetate buffer pH 5 containing 20% ethanol) at 50° C. for 14 hours. TLC detection showed that 40% of $Rb_1$ was converted to ginsenosides with lower sugar contents, indicating that there are ginsenoside glycosidases in almond.

EXAMPLE 5

Preparation of Mixed Ginsenosides and Ginseng Preparations with Higher Contents of Rare Ginsenosides by Ginsenoside Glycosidases

5.1 Preparation of Mixed Ginsenosides with Higher Contents of Rare Ginsenosides 4 g of mixed ginsenosides from ginseng leaves were dissolved in 100 ml of 0.01 M acetate buffer pH 5 and 100 ml of the enzyme solution from *A. oryzae* prepared in section 1.2 of Example 1 was added. The reaction was carried out at 30° C. for 4 hours and then extracted twice with 100 ml of water-saturated butanol. The butanol phases were combined and evaporated to dryness under reduced pressure. 3.3 g of ginsenosides were obtained. TLC detection showed that the contents of rare ginsenosides $Rg_3$, $Rg_2$, Rh2, and $Rh_1$ were increased several ten-folds.

5.2 Preparation of Ginseng Preparation with Higher Contents of Rare Ginsenosides To 4 g of ginseng powder 4 ml 20% ethanol and 4 ml of the enzyme solution from *A. oryzae* prepared in section 1.2 of Example 1 were added. The reaction was carried out at 30° C. for 12 hours and then evaporated to dryness under reduced pressure. A ginseng preparation with higher contents of rare ginsenosides was obtained. TLC detection showed that the contents of rare ginsenosides $Rg_3$, $Rg_2$, $Rh_2$, and $Rh_1$ were increased several ten folds.

5.3 The Chemical Structures of Ginsenosides Obtained from Enzyme Reaction

Ginsenosides Rd, $Rg_3$, $F_2$, Rh2, C-K and aglycone which were obtained from enzymatic conversion of protopanaxadiol-type ginsenosides and ginsenosides $Rg_1$, $Rg_2$, $Rh_1$ and aglycone which were obtained from protopanaxatriol-type ginsenosides by enzymatic conversion were subjected to silica gel columns and eluted with different ratios of chloroform and methanol as described in China Ginseng, Zhang Shuchen (ed.), Shanghai Educational Press, 1992, pages 108-110, to isolate various single ginsenosides which were purified by recrystallization.

The 20(S) and 20(R) forms of ginsenosides $Rg_3$, $Rg_2$, $Rh_2$, and $Rh_1$ were separated by HPLC using a Waters Model-520 with Detector of Waters Programmable Multiwavelength at 203 nm, C-18 column, and the mobile phase is acetonitrile:ethanol (6:4).

The structure of each ginsenoside which was purified from the enzyme reaction was detected by Nuclear Magnetic Resonance (NMR) using Bruker DR X 400 with $d_5$-pyridine as solvent and detected by Mass Spectrometry using JEOL DX X 400 instrument and bombarding the sample with fast atom bombardment mass spectrometry (FAB-MS).

The mass spectra data, $^1$H-NMR, and $^{13}$C-NMR spectra data of ginsenosides Rd, $Rg_3$, $F_2$, Rh2, C-K, $Rg_1$, $Rg_2$, $Rh_1$ and aglycone which were obtained from the enzyme reaction were identical to those disclosed in prior art (such as J. H. Park et al., A new processed ginseng with fortified activity in Advances in Ginseng Research-Proceedings of the 7$^{th}$ International Symposium on Ginseng, Sep. 22-25, 1998, p146-159; Tanak O., Kasai R.: (1984), Saponins of ginseng and related plants in Progress in the Chemistry of Organic Natural Products (Herz W., Grisebach H., Kirby G. W., Tamm Ch., eds), Vol. 46, pl-65). The $^{13}$C-NMR spectra data were shown in Table 12. As shown in Table 12, ginsenosides Rd, $F_2$, C-K and $Rg_1$ which are produced by the enzyme reaction are ginsenosides in 20(S) form, while $Rg_3$, $Rg_2$, $Rh_2$ and $Rh_1$ obtained by the enzyme reaction are both in 20(S) form and in 20(R) form. These data indicate that ginsenosides Rd, $F_2$, C-K and $Rg_1$ produced in the enzyme reaction are mainly in 20(S) form, while the $Rg_3$, $Rg_2$, $Rh_2$ and $Rh_1$ produced in the enzyme reaction are mixtures of 20(S) and 20(R) forms. The structures of 20(S)-ginsenoside and 20(R)-ginsenoside are shown in FIG. 5.

TABLE 12

Chemical shifts in $^{13}$C-NMR spectra of ginsenosides from enzyme reaction

| Carbon atom # | Protopanaxadiol (PPD)-type ginsenosides | | | | | | | | Protopanaxatriol (PPT)-type ginsenosides | | | | | |
|---|---|---|---|---|---|---|---|---|---|---|---|---|---|---|
| | Rd | 20(S)-Rg3 | 20(R)-Rg3 | F2 | C—K | 20(S)-Rh2 | 20(R)-Rh2 | Aglycone | Rg1 | 20(S)-Rg2 | 20(R)-Rg2 | 20(S)-Rh1 | 20(R)-Rh1 | Aglycone |
| 1 | 39.2 | 39.4 | 39.5 | 39.1 | 39.2 | 39.3 | 39.4 | 39.0 | 39.5 | 39.4 | 39.6 | 39.3 | 39.6 | 39.2 |
| 2 | 26.7 | 27.3 | 27.3 | 26.9 | 26.9 | 27.3 | 27.0 | 28.0 | 27.7 | 28.0 | 27.9 | 27.9 | 27.8 | 28.1 |
| 3 | 88.6 | 88.9 | 88.9 | 88.9 | 88.9 | 89.0 | 89.0 | 78.6 | 78.7 | 78.4 | 78.4 | 78.6 | 78.5 | 78.4 |
| 4 | 39.6 | 40.3 | 39.7 | 39.7 | 39.7 | 40.2 | 39.9 | 39.6 | 40.1 | 40.2 | 40.2 | 40.3 | 40.3 | 40.2 |
| 5 | 56.4 | 56.8 | 56.4 | 56.4 | 56.4 | 56.6 | 56.6 | 56.4 | 61.3 | 60.8 | 61.5 | 61.4 | 61.2 | 61.7 |
| 6 | 18.4 | 18.7 | 18.5 | 18.4 | 18.4 | 18.6 | 18.7 | 18.7 | 77.8 | 74.8 | 76.9 | 78.0 | 77.9 | 67.6 |
| 7 | 35.3 | 36.1 | 35.6 | 35.1 | 35.2 | 36.1 | 35.4 | 35.3 | 44.9 | 45.6 | 45.0 | 45.2 | 45.0 | 47.4 |
| 8 | 40.0 | 39.2 | 39.5 | 40.0 | 40.0 | 37.2 | 40.3 | 40.0 | 41.0 | 41.0 | 41.0 | 41.1 | 41.0 | 41.0 |
| 9 | 50.2 | 50.7 | 50.1 | 50.2 | 50.2 | 50.6 | 50.6 | 50.4 | 49.9 | 50.1 | 50.1 | 50.2 | 50.1 | 50.1 |
| 10 | 36.9 | 39.9 | 36.9 | 37.0 | 37.0 | 39.9 | 37.2 | 37.2 | 39.5 | 30.6 | 39.6 | 39.6 | 39.6 | 39.3 |
| 11 | 30.7 | 32.2 | 32.1 | 30.8 | 30.8 | 32.3 | 32.3 | 31.7 | 30.8 | 30.6 | 32.0 | 32.0 | 32.0 | 31.9 |
| 12 | 70.2 | 71.2 | 70.9 | 70.1 | 70.1 | 71.2 | 71.1 | 70.8 | 70.3 | 70.3 | 70.9 | 71.0 | 70.9 | 70.9 |
| 13 | 49.4 | 48.9 | 49.2 | 49.4 | 49.4 | 48.8 | 49.3 | 48.5 | 48.9 | 50.6 | 48.7 | 48.2 | 48.7 | 48.1 |
| 14 | 51.4 | 51.9 | 51.8 | 51.4 | 51.4 | 51.9 | 52.0 | 51.6 | 51.3 | 51.3 | 51.6 | 51.5 | 51.6 | 51.6 |
| 15 | 30.8 | 31.6 | 31.4 | 30.9 | 30.9 | 31.5 | 31.7 | 31.8 | 30.6 | 30.6 | 31.6 | 31.8 | 31.6 | 31.3 |
| 16 | 26.7 | 26.9 | 26.6 | 26.6 | 26.6 | 26.9 | 26.9 | 26.4 | 26.5 | 26.5 | 26.6 | 27.1 | 26.6 | 26.8 |
| 17 | 51.6 | 54.9 | 50.6 | 51.8 | 51.8 | 55.0 | 50.9 | 54.6 | 51.5 | 54.0 | 50.4 | 54.7 | 50.4 | 54.6 |
| 18 | 16.3 | 16.7 | 16.6 | 16.3 | 16.3 | 17.0 | 16.1 | 16.3 | 17.4 | 17.4 | 17.3 | 17.3 | 17.3 | 17.5 |
| 19 | 15.9 | 16.4 | 15.8 | 15.9 | 15.9 | 16.6 | 16.6 | 15.9 | 17.4 | 17.4 | 17.6 | 17.6 | 17.6 | 17.4 |
| 20 | 83.7 | 73.2 | 73.0 | 83.3 | 83.3 | 73.1 | 73.2 | 72.9 | 83.3 | 73.2 | 73.0 | 73.0 | 73.0 | 72.9 |
| 21 | 22.4 | 26.9 | 22.0 | 22.4 | 22.3 | 27.0 | 22.9 | 26.9 | 22.3 | 26.5 | 22.6 | 26.8 | 22.6 | 26.9 |
| 22 | 36.0 | 35.5 | 43.3 | 36.1 | 36.1 | 25.3 | 43.5 | 36.0 | 35.9 | 35.8 | 43.1 | 35.8 | 43.1 | 35.7 |
| 23 | 23.2 | 23.2 | 22.8 | 23.2 | 23.2 | 23.2 | 22.8 | 22.9 | 23.2 | 23.0 | 22.6 | 22.9 | 22.6 | 22.8 |
| 24 | 125.9 | 126.5 | 126.1 | 125.9 | 125.9 | 126.5 | 126.3 | 126.2 | 125.8 | 125.9 | 125.9 | 126.3 | 125.9 | 126.3 |
| 25 | 130.9 | 130.8 | 130.8 | 130.9 | 130.8 | 130.9 | 130.9 | 130.6 | 130.9 | 130.9 | 130.6 | 130.6 | 130.6 | 130.6 |
| 26 | 25.8 | 25.8 | 25.6 | 25.7 | 25.7 | 26.0 | 26.0 | 25.8 | 25.8 | 25.7 | 25.8 | 25.8 | 25.8 | 25.8 |
| 27 | 17.8 | 17.7 | 17.7 | 17.7 | 17.7 | 17.8 | 17.9 | 17.6 | 17.7 | 17.6 | 17.6 | 17.6 | 17.6 | 17.7 |
| 28 | 28.0 | 28.3 | 28.1 | 28.2 | 28.2 | 28.3 | 28.4 | 28.5 | 31.6 | 32.0 | 31.6 | 31.7 | 31.6 | 32.0 |
| 29 | 16.5 | 16.1 | 16.2 | 16.3 | 16.3 | 16.0 | 16.8 | 16.3 | 16.2 | 17.3 | 16.3 | 16.4 | 16.3 | 16.7 |
| 30 | 17.3 | 17.3 | 17.2 | 17.3 | 17.3 | 17.2 | 17.5 | 17.0 | 17.2 | 17.3 | 17.0 | 16.9 | 17.0 | 17.0 |
| 3-C Glc | | | | | | | | | 6-C Glc | | | | | |
| 1' | 105.0 | 103.4 | 103.7 | 106.9 | | 107.1 | 107.1 | | 105.6 | 102.4 | 102.0 | 105.7 | 105.8 | |
| 2' | 83.4 | 83.4 | 83.5 | 75.7 | | 75.8 | 76.0 | | 75.4 | 79.1 | 79.3 | 75.5 | 75.4 | |
| 3' | 78.2 | 78.2 | 78.2 | 79.2 | | 78.7 | 78.9 | | 80.0 | 80.0 | 80.0 | 80.0 | 75.6 | |
| 4' | 71.6 | 71.6 | 71.6 | 71.6 | | 72.2 | 72.1 | | 71.6 | 71.6 | 72.9 | 71.9 | 71.7 | |
| 5' | 78.0 | 78.0 | 78.0 | 78.1 | | 78.0 | 78.4 | | 79.4 | 79.4 | 78.4 | 79.5 | 79.5 | |
| 6' | 62.7 | 62.7 | 62.7 | 62.8 | | 62.3 | 63.3 | | 62.9 | 62.9 | 62.9 | 63.1 | 62.9 | |
| Glc | | | | | | | | | Rha- | Rha- | | | | |
| 1" | 105.8 | 105.8 | 105.6 | | | | | | | 102.5 | 102.4 | | | |
| 2" | 77.0 | 76.9 | 76.9 | | | | | | | 72.8 | 72.9 | | | |
| 3" | 79.1 | 78.5 | 78.5 | | | | | | | 72.8 | 72.8 | | | |
| 4" | 71.6 | 71.9 | 71.7 | | | | | | | 74.6 | 74.6 | | | |
| 5" | 78.1 | 78.1 | 78.1 | | | | | | | 69.9 | 69.9 | | | |
| 6" | 62.7 | 62.7 | 62.7 | | | | | | | 19.2 | 19.2 | | | |

TABLE 12-continued

Chemical shifts in $^{13}$C-NMR spectra of ginsenosides from enzyme reaction

| Carbon atom # | Protopanaxadiol (PPD)-type ginsenosides | | | | | | | | Protopanaxatriol (PPT)-type ginsenosides | | | | | |
|---|---|---|---|---|---|---|---|---|---|---|---|---|---|---|
| | Rd | 20(S)-Rg3 | 20(R)-Rg3 | F2 | C—K | 20(S)-Rh$_2$ | 20(R)-Rh$_2$ | Agly-cone | Rg1 | 20(S)-Rg2 | 20(R)-Rg2 | 20(S)-Rh1 | 20(R)-Rh1 | Agly-cone |
| 20-C Glc | | | | | | | | | | | | | | |
| 1' | 98.1 | | | 98.2 | 98.3 | | | | 98.1 | | | | | |
| 2' | 75.0 | | | 75.1 | 75.1 | | | | 74.8 | | | | | |
| 3' | 78.1 | | | 78.7 | 78.7 | | | | 78.8 | | | | | |
| 4' | 71.6 | | | 71.3 | 71.5 | | | | 71.4 | | | | | |
| 5' | 78.1 | | | 78.2 | 78.1 | | | | 77.8 | | | | | |
| 6' | 62.7 | | | 62.7 | 62.7 | | | | 62.9 | | | | | |

What is claimed is:

1. An isolated ginsenoside glycosidase I, having a molecular weight of 51,000 Daltons by SDS polyacrylamide gel electrophoresis, a pH optimum of 4-6 and a temperature optimum of 30-40 degrees C. that hydrolyzes ginsenosides Rb1, Rb2, Rc or Rd to produce aglycone and one or more of ginsenosides F2, C-K and Rh2.

2. The isolated ginsenoside glycosidase I according to claim 1, prepared by a method comprising:
   a) culturing *A. niger* cells in a medium containing ginseng extract and wheat bran extract to obtain a cultured medium;
   b) removing the *A. niger* cells from the cultured medium to obtain a supernatant;
   c) mixing the supernatant with ammonium sulfate powder to obtain a first solution having an ammonium sulfate concentration of 65%;
   d) storing the first solution overnight to allow protein precipitation;
   e) collecting the protein thus precipitated;
   f) resuspending the precipitated protein in distilled water to obtain a second solution;
   g) dialyzing the second solution against 0.01 M acetate buffer at pH 5.0, to produce a sample containing ginsenoside glycosidase I; and
   h) absorbing the sample containing ginsenoside glycosidase I to DEAE-cellulose DE-52 resin, eluting the ginsenoside glycosidase I-absorbed resin with a gradient of NaCl solution and obtaining purified ginsenoside glycosidase at 0.12 M NaCl concentration.

3. A method of preparing a ginseng product having ginsenosides F2, C-K and Rh2 comprising reacting an isolated ginsenoside glycosidase I having a molecular weight of 51,000 Daltons by SDS gel electrophoresis, a pH optimum of 4-6 and a temperature optimum of 30-40 degrees C. with ginsenosides Rb1, Rb2, Rc or Rd to produce the ginseng product.

4. An isolated ginsenoside glycosidase II, having a molecular weight of 90,000 Daltons by SDS polyacrylamide gel electrophoresis, a pH optimum of 4-7 and a temperature optimum of 30-40 degrees C. that hydrolyzes ginsenosides Rb1, Rb2 or Rc to produce one or more of ginsenosides Rd and Rg3 and hydrolyzes Rd to produce ginsenoside Rg3.

5. The isolated ginsenoside glycosidase II according to claim 4, prepared by a method comprising:
   a) culturing *A. niger* cells in a medium containing ginseng extract and wheat bran extract to obtain a cultured medium;
   b) removing the *A. niger* cells from the cultured medium to obtain a supernatant;
   c) mixing the supernatant with ammonium sulfate powder to obtain a first solution having an ammonium sulfate concentration of 65%;
   d) storing the first solution overnight to allow protein precipitation;
   e) collecting the protein thus precipitated;
   f) resuspending the precipitated protein in distilled water to obtain a second solution;
   g) dialyzing the second solution against 0.01 M acetate buffer at pH 5.0, to produce a sample containing ginsenoside glycosidase II; and
   h) absorbing the sample containing ginsenoside glycosidase I to DEAE-cellulose DE-52 resin, eluting the ginsenoside glycosidase II-absorbed resin with a gradient of NaCl solution and obtaining purified ginsenoside glycosidase at 0.18 M NaCl concentration.

6. A method of preparing a ginseng product having ginsenoside Rd and Rg3 comprising reacting an isolated ginsenoside glycosidase II having a molecular weight of 90,000 Daltons by SDS gel electrophoresis, a pH optimum of 5-7 and a temperature optimum of 30-40 degrees C. with ginsenosides Rb1, Rb2 or Rc to produce the ginseng product.

7. A method of preparing a ginseng product having ginsenoside Rg3 comprising reacting an isolated ginsenoside glycosidase II having a molecular weight of 90,000 Daltons by SDS gel electrophoresis, a pH optimum of 5-7 and a temperature optimum of 30-40 degrees C. with ginsenoside Rd to produce the ginseng product.

8. An isolated ginsenoside glycosidase III, having a molecular weight of 34,000 Daltons by SDS polyacrylamide gel electrophoresis, a pH optimum of 4-5 and a temperature optimum of 30-45 degrees C. that hydrolyzes ginsenoside Rd to ginsenoside C-K.

9. The isolated ginsenoside glycosidase III according to claim 8, prepared by a method comprising:
   a) culturing *A. niger* cells in a medium containing ginseng extract and wheat bran extract to obtain a cultured medium;
   b) removing the *A. niger* cells from the cultured medium to obtain a supernatant;
   c) mixing the supernatant with ammonium sulfate powder to obtain a first solution having an ammonium sulfate concentration of 65%;
   d) storing the first solution overnight to allow protein precipitation;
   e) collecting the protein thus precipitated;

f) resuspending the precipitated protein in distilled water to obtain a second solution;

g) dialyzing the second solution against 0.01 M acetate buffer at pH 5.0, to produce a sample containing ginsenoside glycosidase III; and h) absorbing the sample containing ginsenoside glycosidase III to Bio-scale Q resin, eluting the ginsenoside glycosidase III-absorbed resin with a mixture Tris buffer with NaCl and obtaining purified ginsenoside glycosidase III.

10. A method of preparing a ginseng product having ginsenoside C-K comprising reacting and isolated ginsenoside glycosidase III having a molecular weight of 34,000 Daltons by SDS gel electrophoresis, a pH optimum of 4-5 and a temperature optimum of 30-45 degrees C. with ginsenoside Rd to produce the ginseng product.

11. An isolated ginsenoside glycosidase composition comprising a) glycosidase I that hydrolyzes ginsenosides Rb1, Rb2, Rc or Rd to produce aglycone and one or more of ginsenosides F2, C-K and Rh2, b) glycosidase II that hydrolyzes ginsenosides Rb1, Rb2 or Rc to produce one or more ginsenoside Rd and Rg3 and hydrolyzes Rd to produce ginsenoside Rg3; and c) glycosidase III that hydrolyzes ginsenoside Rd to ginsenoside C-K, prepared by a method comprising:

a) culturing *A. niger* cells in a medium containing ginseng extract and wheat bran extract to obtain a cultured medium;

b) removing the *A. niger* cells from the cultured medium to obtain a supernatant;

c) mixing the supernatant with ammonium sulfate powder to obtain a first solution having an ammonium sulfate concentration of 65%;

d) storing the first solution overnight to allow protein precipitation;

e) collecting the protein thus precipitated;

f) resuspending the precipitated protein in distilled water to obtain a second solution;

g) dialyzing the second solution against 0.01 M acetate buffer at pH 5.0, to produce a sample containing the ginsenoside glycosidase composition.

12. A method of producing a ginsenoside composition comprising reacting the ginsenosidase composition of claim 11 with Rb at 40 degrees C. at pH 5.0 for 18 hours to obtain the ginsenoside composition comprising 5% Rd, 50% F2, 6% Rh2, 34% C-K and 5% aglycone.

13. An isolated ginsenoside alpha-rhamnosidase, having a molecular weight of 53,000 Daltons by SDS polyacrylamide gel electrophoresis, a pH optimum of 5 and a temperature optimum of 30-50 degrees C. that hydrolyzes ginsenosides Re and Rg2 to ginsenosides Rg1 and Rh1, respectively.

14. The isolated ginsenoside alpha-rhamnosidase according to claim 13, prepared by a method comprising:

a) culturing *A. oryzae* cells in a medium containing ginseng extract and wheat bran extract to obtain a cultured medium;

b) removing the *A. oryzae* cells from the cultured medium to obtain a supernatant;

c) mixing the supernatant with ammonium sulfate powder to obtain a first solution having an ammonium sulfate concentration of 65%;

d) storing the first solution overnight to allow protein precipitation;

e) collecting the protein thus precipitated;

f) resuspending the precipitated protein in distilled water to obtain a second solution containing ginsenoside alpha-rhamnosidase;

g) absorbing the second solution containing the ginsenoside alpha-rhamnosidase to Bio-scale Q2 resin, eluting the ginsenoside alpha-rhamnosidase-absorbed resin with a mixture of Tris buffer and NaCl and obtaining purified ginsenoside alpha-rhamnosidase.

15. A method of preparing a ginseng product having ginsenoside Rg1, comprising reacting an isolated ginsenoside alpha-rhamnosidase having a molecular weight of 53,000 Daltons by SDS polyacrylamide gel electrophoresis, a pH optimum of 5 and a temperature optimum of 30-50 degrees C. with ginsenoside Re to produce the ginseng product.

16. A method of preparing a ginseng product having ginsenoside Rha1, comprising reacting an isolated ginsenoside alpha-rhamnosidase having a molecular weight of 53,000 Daltons by SDS polyacrylamide gel electrophoresis, a pH optimum of 5 and a temperature optimum of 30-50 degrees C. with ginsenoside Rg2 to produce the ginseng product.

* * * * *